United States Patent [19]
Huh et al.

[11] Patent Number: 5,986,025
[45] Date of Patent: Nov. 16, 1999

[54] METALLOCENE COMPOUND AND METHOD FOR PRODUCING POLYMER BY USING IT AS POLYMERIZATION CATALYST

[75] Inventors: Wan-soo Huh, Seoul; Dong-ho Lee; Seok-kyun Noh, both of Daegu, all of Rep. of Korea

[73] Assignee: Korea Academy of Industrial Technology, Seoul, Rep. of Korea

[21] Appl. No.: 08/852,040

[22] Filed: May 6, 1997

Related U.S. Application Data

[63] Continuation of application No. 08/540,966, Oct. 11, 1995, abandoned.

[30] Foreign Application Priority Data

Oct. 13, 1994 [KR] Rep. of Korea ................... 94-26500

[51] Int. Cl.$^6$ ......................... C08F 4/64; C07F 17/00
[52] U.S. Cl. ................. 526/119; 526/115; 526/116; 526/127; 526/129; 526/131; 526/160; 526/352; 526/943; 556/11; 556/19; 556/43; 556/53
[58] Field of Search ..................... 526/119, 127, 526/129, 160, 943, 352, 115, 116, 131; 556/11, 19, 43, 53

[56] References Cited

U.S. PATENT DOCUMENTS

| | | | |
|---|---|---|---|
| 4,931,417 | 6/1990 | Miya | 502/117 |
| 5,017,714 | 5/1991 | Welborn, Jr. | 556/12 |
| 5,318,935 | 6/1994 | Canich | 502/117 |
| 5,329,033 | 7/1994 | Spaleck et al. | 556/53 |
| 5,399,636 | 3/1995 | Alt et al. | 526/129 |
| 5,401,817 | 3/1995 | Palackal | 526/127 |
| 5,510,502 | 4/1996 | Sugano et al. | 556/11 |

FOREIGN PATENT DOCUMENTS 0284708 10/1988 European Pat. Off. .

OTHER PUBLICATIONS

Lee et al,, Macromol. Rapid Comm, 16 ,265–268 (Apr. 1, 1995).
"Journal of Organometallic Chemistry, 369 (1989) 359–370".
"Chemistry Letters,pp. 1853–1856, 1989".
Abstract of US 4,931,437, Miya et al. (abstracting Service not identified).
Sinn, H. et al. Adv. Organomet.Chem. 18, 99, 123–129 Acad. Press, NY, 1980.
Hawley's Condensed Chemical Dictionary, 11th Ed., 1987 Van Nostrand Reinhold, New York, inside front cover.

*Primary Examiner*—David W. Wu
*Attorney, Agent, or Firm*—Ladas & Parry

[57] ABSTRACT

A novel metallocene compound and a method for producing a polymer by using the metallocene as a polymerization catalyst. The present catalyst includes a neutral metallocene compound, a cationic metallocene compound, and the compound supported catalyst. The present catalyst can be used to produce a polymer having a characteristic structure and physical properties.

27 Claims, No Drawings

METALLOCENE COMPOUND AND METHOD FOR PRODUCING POLYMER BY USING IT AS POLYMERIZATION CATALYST

This is a continuation of application Ser. No. 08/540,966 filed Oct. 11, 1995 now abandoned.

FIELD OF THE INVENTION

The present invention relates to a novel metallocene compound having heteroatomic bridge and a method for producing polymer by using it as polymerization catalyst.

BACKGROUND OF THE INVENTION

Dong-ho Lee, Keun-byoung Yoon and Wan-su Huh, Macromol. Rapid Commun., 15 841 (1994) describes the use of cyclodextrin as a support of a polymerization catalyst. Also S. Ciruelos, T. Cuenca, P. Gomez-sal, A. Manazanero and P. Royo, Orgametallics, 14, 177 (1995) describes the synthesis method of tetramethyl disiloxanebis ($\eta^5$-cyclopentadienyl) zirconium dichloride, and their structure identification. However, the use of the above dichloride as a polymerization catalyst is not suggested.

SUMMARY OF THE INVENTION

It is an object of the present invention to provide a metallocene compound having heteroatomic bridge which can be used as a catalyst for producing a polymer.

It is another object of the present invention to provide a method for producing a homopolymer or copolymer which comprises homopolymerizing or copolymerizing a vinyl monomer by using a metallocene compound prepared as such or a catalyst prepared by supporting the metallocene compound on a support or a catalyst bonded to a support.

DETAILED DESCRIPTION OF THE INVENTION

The present invention relates to a novel metallocene compound having a heteroatomic bridge and a method for producing a polymer by using it as polymerization catalyst.

Generally, there have been found that various kinds of metallocene compounds can be used for the production of a polymer. A metallocene compound having a heteroatomic bridge according to the present invention, when it is used as a polymerization catalyst, can give the polymer a specific structure and physical properties since it has a specific structure and a polymerization property.

The present metallocene compound having a heteroatomic bride (hereinafter, referred to as HBM compound) is represented by the formula I or II

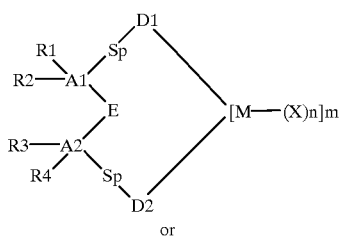

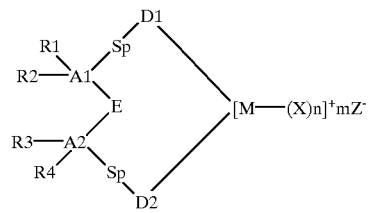

in which
M is Group 3–10 metal element of the Periodic Table, transition metal element or lanthanide, D1 and D2, independently of one another, are unsubstituted or substituted cyclopentadienyl or cyclopentadienyl derivatives or similar compounds which are capable of $\eta^5$ bonding with M, for example indenyl and fluorenyl, A1 and A2, independently of one another, are Group IV B element of the Periodic Table, and A1 and D1 or A2 and Y2 may have spacer between them where spacer is carbon, oxygen, nitrogen or phosphorus, E is heteroatom, preferably nitrogen, oxygen, phosphorus or sulfur, and forming a site between D1 and D2 ligand, R1 to R4, independently of one another, are a group selected from the group consisting of hydrogen, alkyl, aryl, silyl, alkoxy, arlyoxy, siloxy and halogen, alone or combination thereof, or -Sp-Sup (wherein Sp is spacer, and Sup is support), X is a group selected from the group consisting of hydrogen, alkyl, aryl, silyl, alkoxy, arlyoxy, siloxy and halogen, alone or combination thereof, n is 0 to 4 depending on kinds of metal and valency, and m is 1 or 2, and if m is 2, M is bonded to either D1 or D2.

In the formula II, Z is a non-coordinating anion which is not coordinated or very weakly coordinated to a cationic metal portion having D not to inhibit a lewis base from reacting with the metal portion having D of cation, preferably [BQ1Q2Q3Q4]⁻ wherein B is trivalent Boron; Q1 to Q4, independently of one another, are a radical selected from the group consisting of hydrogen anion, dialkylamido, alkoxide, aryloxide, hydrogen carbyl, substituted hydrogencarbyl and organic metalloid; and one of Q1 to Q4 can be halide.

An HBM compound according to the present invention is prepared in the following three steps:

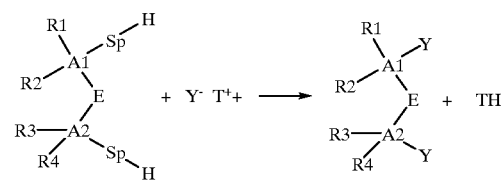

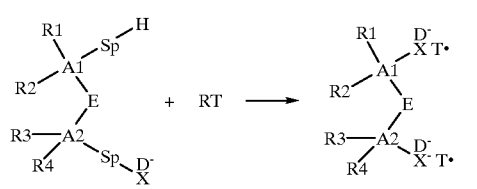

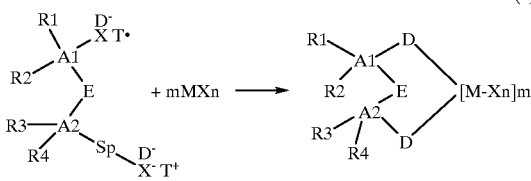

(3)

in which

A1, A2, E, R1, R2, R3, R4 and Sp are as defined in the formula I or II,

D is D1 or D2,

H is halogen atom,

D⁻ is D1 or D2 anion as defined in formula I or II,

T⁺ is alkali metal cation,

R is alkyl or alkoxy, and

T is alkali metal or thallium.

An HBM compound according to the present invention can be supported on a conventional support in order to be used as a polymerization catalyst. For example, compounds of the formula I or II are directly supported on a dehydrated support. Examples of a support are silica, alumina, magnesium chloride, zeolite, aluminum phosphate or zirconia as well as starch and cyclodextrin. Supported catalyst is prepared by dipping a dehydrated support in the solution of the formula I or II. In addition to the above method wherein the compound of the formula II is directly supported on a support, cationic HBM (compound of the formula II) supported catalyst can be prepared by supporting a neutral HBM compound (compound of the formula I) on a support and activating with a boron compound. The boron compound cocatalyst is $[R5R6R7C]^+[BQ1Q2Q3Q4]^-$ or $[HNR8R9R10]^+[BQ1Q2Q3Q4]^-$ wherein R5 to R10 are hydrogen, alkyl, aryl, alkoxy, silyl or siloxy, and B and Q1 to Q4 are as defined above.

Another method for producing polymerization catalyst is to modify a support and then produce a metallocene compound according to the present invention together with a support as shown in the following reaction scheme

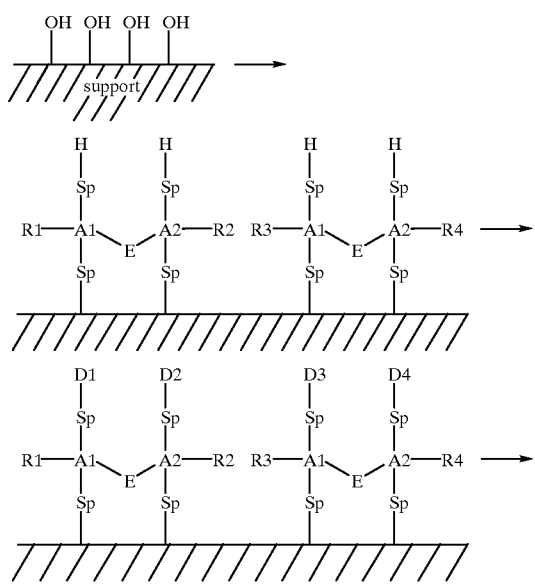

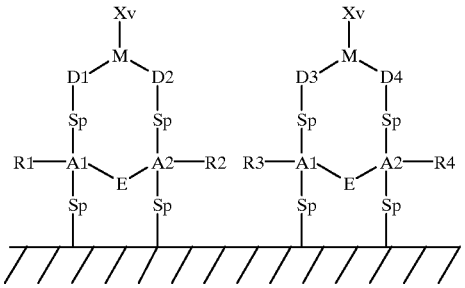

in which

A1, E, M, D1, D2 and $(X)_n$ are as defined in the above, and D3 and D4 are identical or different from D1 and D2, and Sp is spacer linking surface of support with ligand D, and consisting of carbon, oxygen, nitrogen or phosphorus.

In the above scheme, such Sp can be linked one another through a chemical bond having carbon, oxygen, nitrogen and phosphorus.

An HBM compound according to the present invention, or a catalyst wherein an HBM compound is supported on a support or a catalyst wherein an HBM compound is bonded to a modified surface of a support can be used to prepare a homopolymer or copolymer from vinyl monomer by homopolymerization or copolymerization. The vinyl monomer is preferably α-olefin, ethylene, cycloolefin, diene or diolefin, most preferably ethylene or propylene.

The amount of polymerization catalyst used is preferably $10^{-7}$–$10^{-4}$ mole/l, more preferably $10^{-6}$–$10^{-5}$ mole/l, based on the amount of monomer reactant used.

The polymerization temperature is 0–80° C., and preferably 20–60° C.

The HBM compound supported catalyst of the present invention can be used with an organic metal compound as cocatalyst. The organic metal compound is preferably alkylaluminoxane or organic aluminum compound. The alkylaluminoxane is preferably methylaluminoxane or modified methylaluminoxane. The organic aluminum compound is more preferably $AlR_nX_{3-n}$ wherein R is $C_1$–$C_{10}$ alkyl or $C_1$–$C_{10}$ aryl, X is halogen and n is an integer of 1 to 3.

Now, the present invention will be described more specifically with reference to Examples hereinafter, however it should be noted that the present invention is not intended to be restricted within those specific Examples.

In the Examples, the structure and component of the catalyst prepared, and the melting point, crystallization temperature, molecular weight and structure of the catalyst active polymer were measured by the following method.

(1) Structure and Component of the Catalyst

The structure of the catalyst was measured by hydrogen and carbon nuclear magnetic resonance (H-NMR or C-NMR), and the component of the catalyst was analyzed by induction plasma spectrometer.

(2) Polymerization of Ethylene

The polymerization of ethylene was carried out in an glass reactor equipped with an external temperature regulator, a magnetic stirrer and a valve for introducing monomer and nitrogen. The glass reactor was firstly purged with nitrogen. To that reactor were added charged purified toluene and methylaluminoxane as cocatalyst in a necessary amount, sufficiently stirred and saturated with ethylene. Polymerization was initiated by using a necessary amount of catalyst. After a given period of time, polymerization was completed by adding a small amount of methanol. The resulting mixture was poured into a great amount of methanol to which hydrochloric acid had been added. The obtained polymer was washed with water and methanol and then dried under a vacuum.

(3) Activity of Catalyst

The activity of the catalyst was determined by measuring the weight of polyethylene obtained from polymerization, and was shown as kg PE/g Zr-atm-h.

(4) Melting Point and Crystallization Temperature of Polymer

The melting point and crystallization temperature of the polymer were measured by differential scanning calorimeter (DSC) in which a sample is warmed up to 200° C. by 20° C./minute increase, left for 5 minutes and then cooled by 20° C./minute.

(5) Molecular Weight and Structure of Polymer

The molecular weight of the polymer was measured by gel permeation chromatography with elution with benzene trichloride. The structure of the polymer was analyzed by carbon nuclear magnetic resonance (C-NMR).

EXAMPLE 1

Synthesis of Tetramethyl Disiloxanebis ($\eta^5$-cyclo pentadienyl)zirconium dichloride (a) Synthesis of 1,3-Dicyclopentadienyl Tetramethyldisiloxane 10 mmol of 1,3-dichlorotetramethyl disiloxane was dissolved in 50 ml of THF, and 20 mmol of sodium cyclopentadienylide (2.0 M, THF solution) was slowly added to the solution at −78° C. The mixed solution was reacted at room temperature for about 5 hours. After the completion of the reaction, solvent was removed from the mixture. To that mixture hexane was added, and LiCl obtained from the reaction was removed by filtration. The removal of solvent from filtrated solution gave the title product as yellow liquid in a yield of 90%.

(b) Synthesis of Tetramethyl Disiloxanebis ($\eta^5$-cyclopentadienyl) Zirconium Dichloride (i) Synthesis Route Starting from $ZrCl_4$ 10 mmol of 1,3-dicyclopentadienyl tetramethyl disiloxane prepared above was dissolved in 50 ml of THF, 20 mmol of n-butyl lithium was added at −78° C. to the solution, and stirred at room temperature for 3–5 hours to give solution containing a lithium-containing intermediate. The obtained solution was mixed at −78° C. with THF solution in which 20 mmol of $ZrCl_4$ had been dissolved, and the mixed solution was reacted at room temperature for 10–15 hours and after completion of the reaction solvent was removed. To the resulting mixture was added 30 ml of $CH_2Cl_2$, filtered to remove LiCl and added 50 ml of filtrated hexane to recrystallize the product. Recrystallized solid product was recrystallized again in $CH_2Cl_2$ or toluene solution to give the title product in a yield of 50%.

(ii) Synthesis Route Starting from $ZrCl_2Me_2$ 10 mmol 1,3-dicyclopentadienyl tetramethyl disiloxane solution containing the above-described lithium-containing intermediate was prepared by the same method in (a) of Example 1. To the separate flask 20 mmol of $ZrCl_4$ was added to 50 ml of THF; and 40 mmol of methyl lithium was slowly added at −78° C. to give $ZrCl_2Me_2$ solution. The above separately prepared two solutions were mixed at −78° C., stirred for 2–3 hours, reacted at room temperature for 10 hours and then passed through HCl. After completion of passing through HCl, solvent was removed. The final product was separated after a product-separating step and a purifying step.

EXAMPLE 2

Synthesis of Tetramethyl Disiloxanebis ($\eta^5$-cyclo pentadienyl) Zirconium Dimethylate (a) Synthesis Route Starting from $ZrCl_4$ 10 mmol of tetramethyldisiloxane ($\eta^5$-cyclopentadienyl) zirconium dichloride prepared in (b) of Example 1 was dissolved in 50 ml of THF and 20 mmol of methyl lithium was slowly added at −78° C. The mixture was stirred at room temperature for 2–5 hours and solvent was removed and 50 ml of ether was added. LiCl was removed and recrystallized at −30° C. to give the title product as dark brown in a yield of 50%.

(b) Synthesis Route Starting from $ZrCl_2Me_2$

In the method of (b)-(ii) of Example 1, solvent was removed from the reaction solution taken before the passing through HCl; ether was added and filtered to remove LiCl. Filtrated solution was recrystallized at −30° C. to give title product in a yield of 50%.

EXAMPLE 3

Polymerization of Ethylene and Thermal Properties and Structure of the Polyethylene Polymer (1) Properties of the Present Catalyst In order to examine the properties of the present catalyst (HBM), catalytic activity of a few metallocene polymerization catalysts which can be generally used in the polymerization of ethylene, and HBM was measured. The melting point and crystallization temperature of the polyethylene obtained were also measured. The results are summarized in Table 1 and compared with those of commercially available polyethylene.

TABLE 1

Catalytic activity of various catalysts, and thermal properties of polyethylene

| Catalyst System and PE | Catalytic Activity | Melting Point (° C.) | Crystallization Temperature (° C.) |
|---|---|---|---|
| $Cp_2ZrCl_2$—MAO | 73.0 | 133 | 114 |
| $Ind_2ZrCl_2$—MAO | 49.3 | 129 | 110 |
| $Et(Ind)_2ZrCl_2$—MAO | 20.5 | 130 | 117 |
| HBM—MAO | 7.2 | 133 | 116 |
| HBM—MAO* | 20.1 | 117 | 103 |
| HDPE | — | 142 | 102 |
| LLDPE | — | 122 | 102 |
| LDPE | — | 108 | 89 |

(note) catalytic activity: kg PE/g Zr-atm-h
*in the presence of small amount of propylene (2) Thermal Properties of Polymer depending on Polymerization Condition Ethylene can be polymerized by using an HBM catalyst obtained above and methylaluminoxane as cocatalyst in the presence of a small amount of propylene. The effect of the amount of methylaluminoxane and catalyst and the polymerization temperature on the catalytic activity and thermal properties of the polymer was examined; and the results are summarized in Table 2.

TABLE 2

Catalytic activity and thermal properties of polymer depending on the amount of catalyst component in HBM and the polymerization temperature

| [Al]/[Zr] | Temperature (° C.) | Catalytic Activity | Melting Point (° C.) | Crystallization Temperature (° C.) |
|---|---|---|---|---|
| 4000 | 40 | 6.7 | 116 | 99 |
| 7000 | 40 | 14.4 | 117 | 102 |
| 10000 | 40 | 20.1 | 117 | 103 |
| 10000 | 55 | 4.1 | 98 | 84 |
| 15000 | 40 | 16.5 | 119 | 105 |

Catalytic activity: kg PE/g Zr-atm-h

When ethylene was polymerized by using an HBM catalyst prepared by the present invention, polymerization activity was smaller than that of $Cp_2ZrCl_2$, but similar to that of $Et(Ind)_2ZrCl_2$. The melting point and crystallization temperature of the polyethylene obtained by using HBM were similar to those of polymer or HDPE obtained by using another catalyst, while the thermal properties of PE obtained in the presence of a small amount of propylene were similar to those of LLDPE and LDPE. The molecular weight of PE can be controlled in the range of $10^3$–$10^5$, in particular 1,000–500,000 with the change of the catalyst component ratio, polymerization temperature and the amount of hydrogen added. The molecular weight disperse is in the range of 1.5–3.0.

When the polymerization of ethylene was carried out by using HBM catalyst according to the present invention in the presence of α-olefin, chain branch of α-olefin can be formed, which can greatly reduce the melting point of the polymer prepared; and thus processability and thermal adhesiveness are greatly improved.

When HBM catalyst according to the present invention is used, polymerization and copolymerization of ethylene and α-olefin are feasible to be carried out, and therefore a variety of polyolefins can be prepared.

What is claimed is:

1. A metallocene compound represented by the formula I or II:

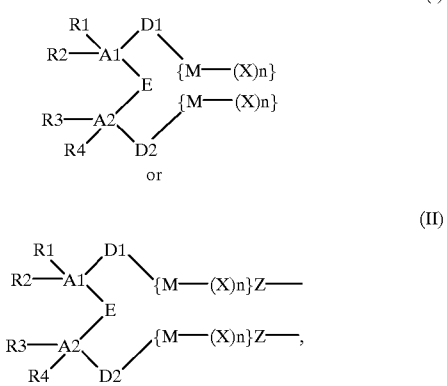

in which
M is a Group 3–10 metal element of the Periodic Table, transition metal element or lanthanide,
D1 and D2, independently of one another, are unsubstituted or substituted cyclopentadienyl, indenyl, or fluorenyl,
A1 and A2, independently of one another, are Group 14 elements of the Periodic Table,
E is oxygen, or sulfur, and forming a site between D1 and D2 ligand,
R1 to R4, independently of one another, are a group selected from the group consisting of hydrogen, alkyl, aryl, silyl, alkoxy, aryloxy, siloxy and halogen, alone or in combination thereof,
X is a group selected from the group consisting of hydrogen, alkyl, aryl, silyl, alkoxy, aryloxy, siloxy and halogen, alone or in combination thereof,
n is 0 to 4 depending on kinds of metal and valency, and
Z is non-coordinating boron anion which is not coordinated or which is very weakly coordinated to cationic metal portion.

2. A method for preparing vinyl polymer comprising adding to a vinyl monomer (i) a metallocene compound as claimed in claim 1 in an amount effective as a catalyst and (ii) an organometallic compound that is used as cocatalyst, and heating the resulting vinyl monomer mixture at a temperature of 20° C. to 60° C.

3. A method according to claim 2, further comprising supporting the metallocene compound on a support selected from the group consisting of silica, alumina, magnesium chloride, zeolite or aluminum phosphates.

4. A method according to claim 2, further comprising bonding the metallocene compound to the surface of a support selected from the group consisting of silica, alumina, magnesium chloride, zeolite or aluminum phosphate.

5. A method according to claim 2, wherein the vinyl monomer is α-olefin, ethylene, cycloolefin, or diene.

6. A method according to claim 2, wherein the organometallic compound is alkylaluminoxane or modified methylaluminoxane.

7. A method according to claim 2, wherein the concentration of catalyst used is in the range from $10^{-7}$ to $10^{-4}$ mole/l.

8. A method according to claim 3, wherein the vinyl monomer is α-olefin, ethylene cycloolefin, or diene.

9. A method according to claim 3, wherein the organometallic compound is alkylaluminoxane or modified methylaluminoxane.

10. A method according to claim 3, wherein the concentration of catalyst used is in the range from $10^{-7}$ to $10^{-4}$ mole/l.

11. A method according to claim 4, wherein the vinyl monomer is α-olefin, ethylene, cycloolefin, or diene.

12. A method according to claim 4, wherein the organometallic compound is alkylaluminoxane or modified methylaluminoxane.

13. A method according to claim 4, wherein the concentration of catalyst used is in the range from $10^{-7}$ to $10^{-4}$ mole/l.

14. A method according to claim 8, wherein the organometallic compound is alkylaluminoxane or modified methylaluminoxane.

15. A method according to claim 8, wherein the concentration of catalyst used is in the range from $10^{-7}$ to $10^{-4}$ mole/l.

16. A method according to claim 11, wherein the organometallic compound is alkylaluminoxane or modified methylaluminoxane.

17. A method according to claim 11, wherein the concentration of catalyst used is in the range from $10^{-7}$ to $10^{-4}$ mole/l.

18. A method for producing homopolymer or copolymer which comprises providing a vinyl monomer, and homopolymerizing or copolymerizing the vinyl monomer by adding to the vinyl monomer a metallocene compound according to claim 1 in an amount effective as a catalyst and an organometallic compound that is used as cocatalyst, and heating the resulting vinyl monomer mixture at a temperature of 20° C. to 60° C.

19. A method according to claim 18, wherein the concentration of catalyst used is in the range from $10^{-7}$ to $10^{-4}$ mole/l.

20. A method according to claim 18, wherein the vinyl monomer is α-olefin, ethylene, cycloolefin, or diene.

21. A method according to claim 18, wherein the organometallic compound is alkylaluminoxane or modified methylaluminoxane.

22. A method according to claim 18, wherein the organometallic compound is an organic aluminum compound represented by the formula $AlR_nX_{3-n}$ (1) where R is $C_1$–$C_{10}$ alkyl or $C_1$–$C_{10}$ aryl, X is halogen, and n is an integer of 1 to 3.

23. A method according to claim 19, wherein the vinyl monomer is α-olefin, ethylene, cycloolefin, or diene.

24. A method according to claim 19, wherein the organometallic compound is alkylaluminoxane or modified methylaluminoxane.

25. A method according to claim 22, wherein the vinyl monomer is α-olefin, ethylene, cycloolefin, or diene.

26. A method for producing homopolymer or copolymer which comprises providing a vinyl monomer, homopolymerizing or copolymerizing the vinyl monomer by adding to the vinyl monomer a metallocene compound as claimed in claim 1 in an amount effective as a catalyst, said metallocene compound being bonded to a support, and an organometallic compound that is used as cocatalyst, and heating the resulting vinyl monomer mixture at a temperature of 20° C. to 60° C.

27. A method according to claim 26, wherein the vinyl monomer is α-olefin, ethylene, cycloolefin, or diene.

* * * * *